(12) United States Patent
Khalili

(10) Patent No.: US 8,777,953 B1
(45) Date of Patent: Jul. 15, 2014

(54) ROCKER MECHANISM

(75) Inventor: Farid B. Khalili, Briarcliff Manor, NY (US)

(73) Assignee: Greatbatch Ltd., Clarence, NY (US)

( * ) Notice: Subject to any disclaimer, the term of this patent is extended or adjusted under 35 U.S.C. 154(b) by 152 days.

(21) Appl. No.: 13/267,049

(22) Filed: Oct. 6, 2011

Related U.S. Application Data

(60) Provisional application No. 61/390,462, filed on Oct. 6, 2010.

(51) Int. Cl.
A61B 17/70 (2006.01)
(52) U.S. Cl.
USPC .......................... 606/86 A; 606/99
(58) Field of Classification Search
USPC .......... 606/86 A, 86 B, 96, 99, 104, 205–208, 606/86 R
See application file for complete search history.

(56) References Cited

U.S. PATENT DOCUMENTS

| | | | |
|---|---|---|---|
| 1,985,108 A | 12/1934 | Rush | |
| 2,112,873 A * | 4/1938 | Wright | 81/343 |
| 4,911,154 A | 3/1990 | Vickers | |
| 5,616,143 A | 4/1997 | Schlapfer et al. | |
| 5,910,141 A | 6/1999 | Morrison et al. | |
| 6,017,342 A | 1/2000 | Rinner | |
| 6,716,218 B2 | 4/2004 | Holmes et al. | |
| 6,739,068 B1 | 5/2004 | Rinner | |
| 6,746,449 B2 * | 6/2004 | Jones et al. | 606/86 A |
| 6,786,931 B2 * | 9/2004 | Hazebrouck | 623/22.42 |
| 6,790,209 B2 | 9/2004 | Beale et al. | |
| 7,014,617 B2 | 3/2006 | Grinberg | |
| 7,081,118 B2 | 7/2006 | Weber et al. | |
| 7,320,689 B2 | 1/2008 | Keller | |
| 7,371,239 B2 | 5/2008 | Dec et al. | |
| 7,431,723 B2 * | 10/2008 | Hazebrouck | 606/99 |
| 7,476,240 B2 | 1/2009 | Raymond et al. | |
| 7,641,653 B2 | 1/2010 | Dalla Betta et al. | |
| 7,744,598 B2 * | 6/2010 | Brumfield et al. | 606/86 A |
| 7,799,031 B2 | 9/2010 | Miller et al. | |
| 2002/0072752 A1 | 6/2002 | Zucherman et al. | |
| 2003/0083747 A1 | 5/2003 | Winkerbottom et al. | |
| 2005/0010213 A1 | 1/2005 | Stad et al. | |
| 2006/0025768 A1 | 2/2006 | Iott et al. | |
| 2008/0004629 A1 | 1/2008 | Nichols et al. | |
| 2008/0243175 A1 * | 10/2008 | Moore et al. | 606/206 |
| 2009/0030420 A1 * | 1/2009 | Runco et al. | 606/99 |
| 2009/0228054 A1 | 9/2009 | Hoffman et al. | |
| 2009/0259262 A1 * | 10/2009 | Nayet | 606/86 A |
| 2009/0281582 A1 * | 11/2009 | Villa et al. | 606/86 A |
| 2010/0069972 A1 | 3/2010 | Jones et al. | |
| 2010/0121385 A1 | 5/2010 | Blain et al. | |
| 2010/0121386 A1 | 5/2010 | Peultier et al. | |

OTHER PUBLICATIONS

Johnson et al., Medtronic CD Horizon Legacy 5.5 Spinal System-Degenerative Surgical Technique.

* cited by examiner

Primary Examiner — Pedro Philogene
Assistant Examiner — Christina Negrellirodrigue
(74) Attorney, Agent, or Firm — Steven W. Winn

(57) ABSTRACT

An orthopedic instrument designed to engage a rod within a fixation element during a surgical procedure is described. The present invention has a distal end portion designed to hold a fixation element such as a pedicle screw while the rod is positioned within the fixation element. The instrument comprises a series of arms which form the grasping and handle portions of the device.

22 Claims, 5 Drawing Sheets

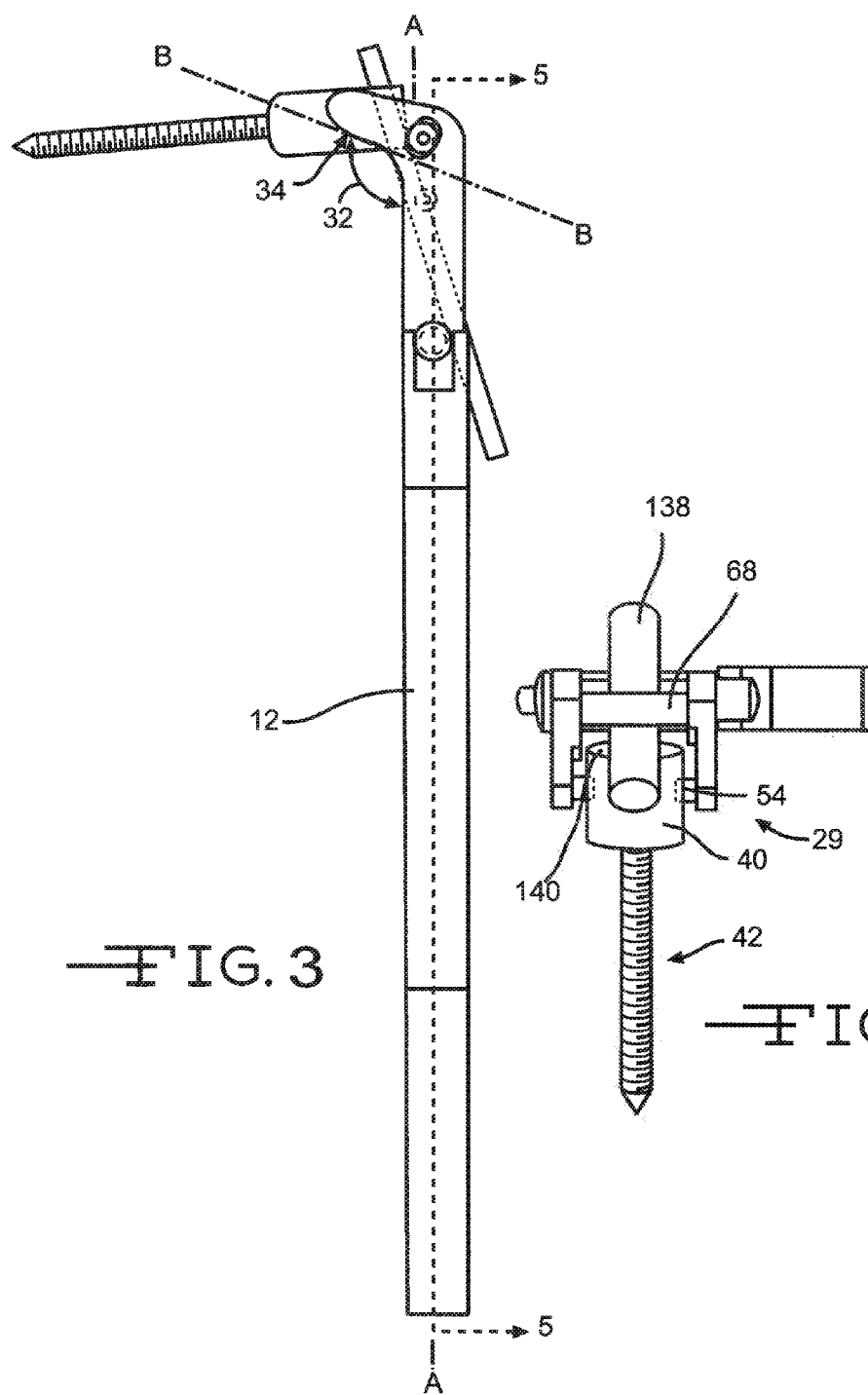

ROCKER MECHANISM

CROSS-REFERENCE TO RELATED APPLICATION

The present application claims priority from U.S. Provisional Application Ser. No. 61/390,462 filed Oct. 6, 2010.

BACKGROUND OF THE INVENTION

1. Field of the Invention

The present invention relates to an apparatus used during orthopedic surgery, more particularly, to an instrument used to position an implant during orthopedic spine surgery.

2. Prior Art

In the field of orthopedic surgical procedures, implanting devices that can support bone or tissue to correct deformities or that will position bone and tissue in such a way as to promote healing are well known. In one such procedure, a plurality of fixation elements, such as a pedicle screw, is first positioned within the spine area. Typically, the pedicle screw is first threaded into a pedicle or other portion of vertebral bone in a vertical alignment along a segment of the spinal column. A rod is then positioned between adjoining fixation elements forming an interconnection therebetween. The combination of rods and fixation elements provides structural support to the spine area.

This same procedure is commonly performed to correct spinal degradation in addition to providing structural support to the spine area. Spinal degradation results in the loss of height between the vertebrae. This loss in height usually results in the pinching of a nerve which routes through the vertebrae, causing pain. In these cases it is often desirable to restore the spacing between the vertebrae. The series of fixation elements and rods are positioned in such a manner as to return the spacing between vertebrae therefore providing pain relief from the compressed nerve.

The spine is comprised of vertebral bones, many of which are not aligned in the same plane. Many times vertebrae are positioned at different elevations and alignments within the body, and as such create complications in establishing proper rod alignment. The process by which a rod is interconnected between two fixation elements is referred to as "rod reduction". During the procedure, the ends of the rod are positioned within channels of opposing fixation elements. Once the ends of the rod are seated within the channels, a setscrew is positioned over the channel, securing the rod therewithin. This procedure is repeated until the desired spine area is secured.

Rod reduction is commonly performed using tools such as pliers or levers to create the necessary pushing and pulling forces that engage the rod with the implant screw. In many cases, a surgeon uses his hands to reduce the rod. In either case, however, neither the use of pliers or levers nor the use of one's hands is optimal. Pliers for example, are prone to slippage and could easily damage adjacent tissue or bone, particularly when trying to align a rod within pedicle screws, which are at different elevations or angulations. One's hands may not impart the appropriate forces required to achieve efficacious rod reduction.

Other instruments were developed to overcome the above noted issues. One such instrument, referred to as a "rocker", is an introducer lever, which resembles a fork with a pair of offset tines. The tines are intended to extend over the suspended rod and under either side of the fixation element. Once in place, the fork handle is rotated toward the rod, thereby forcing the rod and fixation element together. This prior art design requires that the fork tines pass between the fixation element and bone. However, use of a prior art introducer lever device has not proven advantageous, as the fork tines can be prone not to securely engage with the fixation element. As such, these prior art rocker tools may slip during rod reduction, thereby causing possible injury to the patient. Additionally, passing the fork tines between the fixation element and bone may not be possible due to anatomic restrictions. Use of this prior art design also does not resolve slippage issues similar to that observed with pliers and thus may also result in damage to bone or tissue.

Other variations of these devices, commonly referred to as "forceps rockers", have been developed to provide a more secure engagement with the fixation element. However, many of these prior art forceps rocker devices require the use of an additional instrument in concert with the forceps to reduce the rod within the fixation element. Therefore, use of these devices requires utilization of both hands, which prohibits the surgeon from manipulating another device.

Still other prior art devices such as the instrument described in U.S. Pat. No. 5,423,855 to Marienne, have been developed to provide a more secure engagement with the fixation element. The Marienne device comprises a gripping nose with articulating arms that are held in a closed position by a spring biased cap. With this type of prior design, the operator must first open the forceps to pass the mechanism over the head of the fixation element. This design was an improvement over other prior designs with regards to adapting to various anatomic constraints, however, the design does not provide adequate strength to hold the fixation element while reducing the rod, particularly when greater torques are required to properly position the rod between fixation pedicle screws.

Therefore, there is a need for an improved rocker mechanism that is easy to use, is more secure and reduces patient, bone and tissue injury risks. The present invention satisfies these needs and overcomes the problems associated with the prior art. The present invention provides an open position, which allows the device to easily slip over the head of the fixation device. Furthermore, since the present invention provides a more secure engagement with the fixation element, it is capable of generating greater torques in a single hand held instrument. In addition, the present invention provides a slender design that is less invasive and provides improved line of sight during the surgical procedure.

SUMMARY OF THE INVENTION

The present invention provides an orthopedic instrument that is designed to engage a rod within a fixation element during a surgical procedure. The present invention has a distal end portion designed to grasp a fixation element. The distal end portion is actuated by a handle portion located at the instrument's proximal end.

The orthopedic instrument is comprised of a series of arms that are aligned in a parallel orientation. Specifically, the instrument is comprised of a left arm, a right arm and an intermediary arm positioned therebetween. A prong extends from the distal ends of each of the left and intermediary arms that form the fixation element grasping portion of the device. Opposing protrusions extend from the respective inner surfaces of these arms. These protrusions are designed to contact the outer surface of the fixation element.

The right arm of the device forms a handle portion with the opposing left arm. A releasable locking mechanism provides a means for a user to securely grasp the outer surface of the fixation element with the opposing distal end prongs. The locking mechanism comprising a ratchet post and corresponding "V" groove of the proximal end of the left arm enables the prongs to lock into position about the fixation element. The accompanying release mechanism enables separation of the ratchet post from the proximal end of the left arm and therefore allows the handle ends to widen. Once the ratchet post is disengaged with the left arm, the gap between the opposing distal end prongs widens and the connection between the instrument and the fixation element is removed.

Once the opposing prong ends are in position around the outer surface of the fixation element, a rod positioned between the left and intermediary arms can then be urged into position within the fixation element.

BRIEF DESCRIPTION OF THE DRAWINGS

FIG. 3 is a side view of the instrument.
FIG. 4 illustrates a front end view of the instrument.

DETAILED DESCRIPTION OF THE PREFERRED EMBODIMENTS

Figure 1:
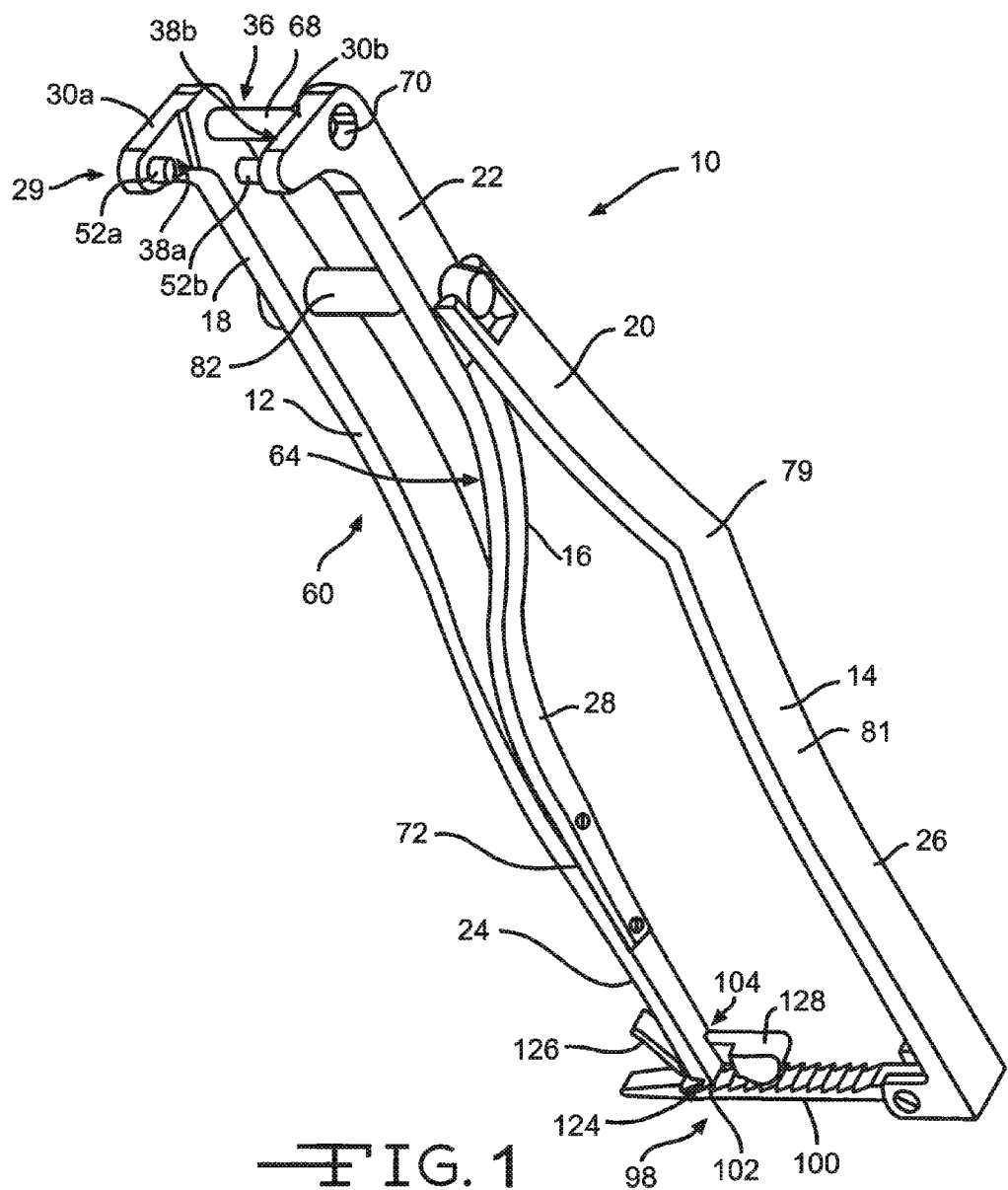
FIG. 1 illustrates a perspective view of the orthopedic instrument of the present invention.
Figure 2:
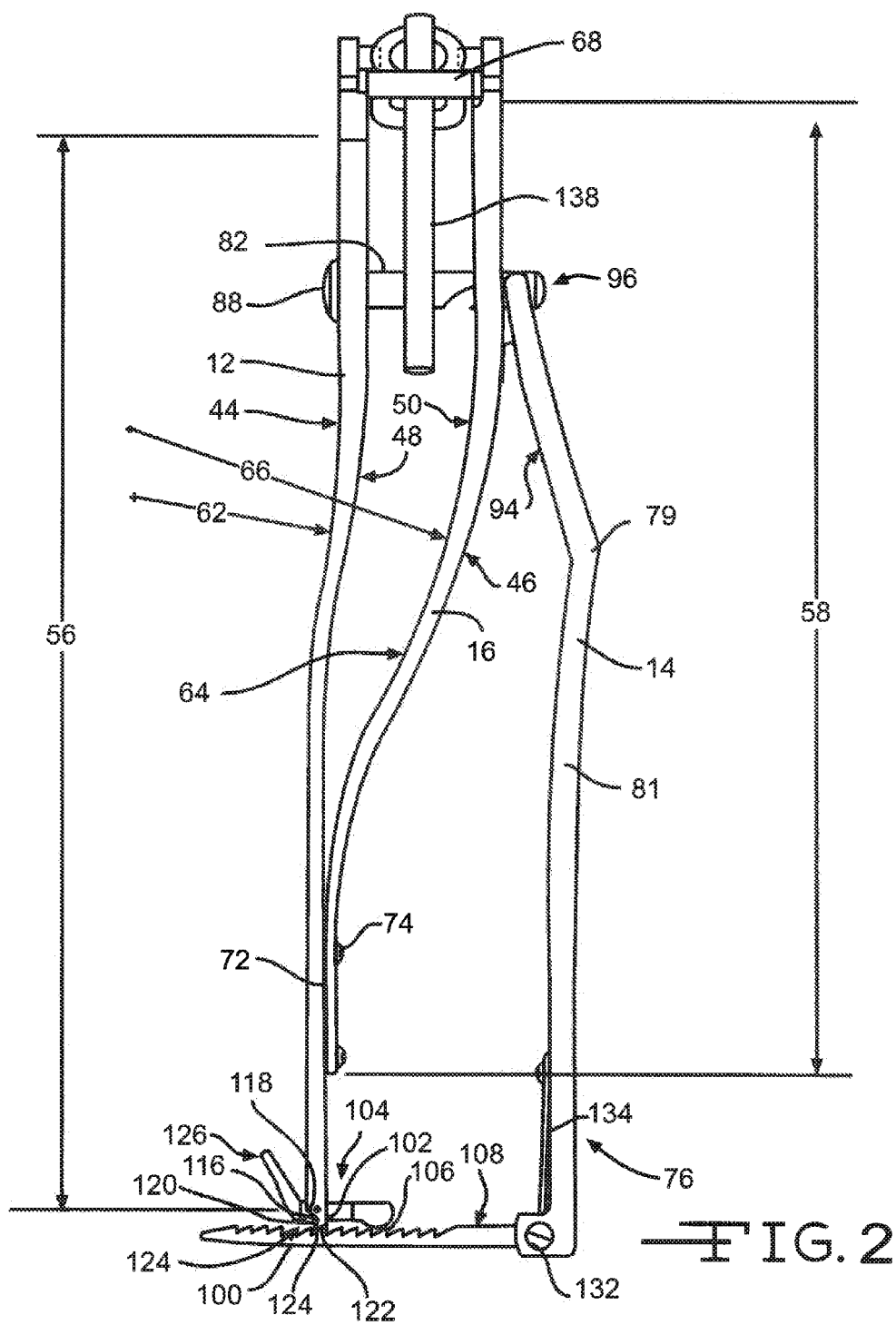
FIG. 2 shows a bottom view of the instrument.

Now referring to the figures, FIGS. 1-6 illustrate embodiments of an orthopedic instrument 10 of the present invention. As illustrated in FIG. 1, the instrument 10 comprises a left arm 12, a right arm 14, and an intermediary arm 16 positioned therebetween. Each of the arms 12, 14, 16 has a distal end portion 18, 20, 22 separated from a proximal end portion 24, 26, 28. The arms are aligned such that the respective distal end portions 18, 20, 22 and proximal end portions 24, 26, 28, are about parallel to each other. It should be noted that the orthopedic instrument 10 of the present invention can be used with either the user's left or right hand and further can be used in an upwardly or downwardly orientation. The terms "left arm" and "right arm" are used only to identify and distinguish between specific features and embodiments of the present invention. In operation, the "right arm" may in fact be positioned on the left and the "left arm" may be positioned on the right. Furthermore, it is contemplated that the preferred embodiments could also be constructed in an inverse relationship. For example, the right arm could also be positioned on the left side and vice versa.

At the distal end of each of the respective left and intermediary arms 12, 16, is positioned a prong portion 30a, 30b. These prong portions 30a, 30b preferably extend from the distal end of the respective left and intermediary arms 12, 16. In a preferred embodiment, these prong portions mirror each other such that their length, width and orientation are similar. However, it is contemplated that the prong portions 30a, 30b may not necessarily mirror each other. For example, the length of the prong portion 30a, may be longer than the opposite prong portion 30b. In addition, the orientation of the respective prong regions 30a, 30b may be different from each other.

The prong portions 30a, 30b are oriented such that they are not parallel with respect to a longitudinal axis A-A. In a preferred embodiment, each of these prong portions 30a, 30b is angled at a prong angle 32 (FIG. 3). The prong angle 32 is herein defined as the angle between longitudinal axis A-A and a tangent line B-B which extends along a bottom surface 34 of the prong portion 30a, 30b. In a preferred embodiment, the prong angle 32 ranges from about 5° to about 50°. Each of the prongs 30a, 30b have a prong angle 32. Although it is preferred that each of the prongs 30a, 30b have a prong angle 32 with about the same degree of angle, it is contemplated that the prong angle 32 may differ between prongs 30a, 30b.

Figure 6:
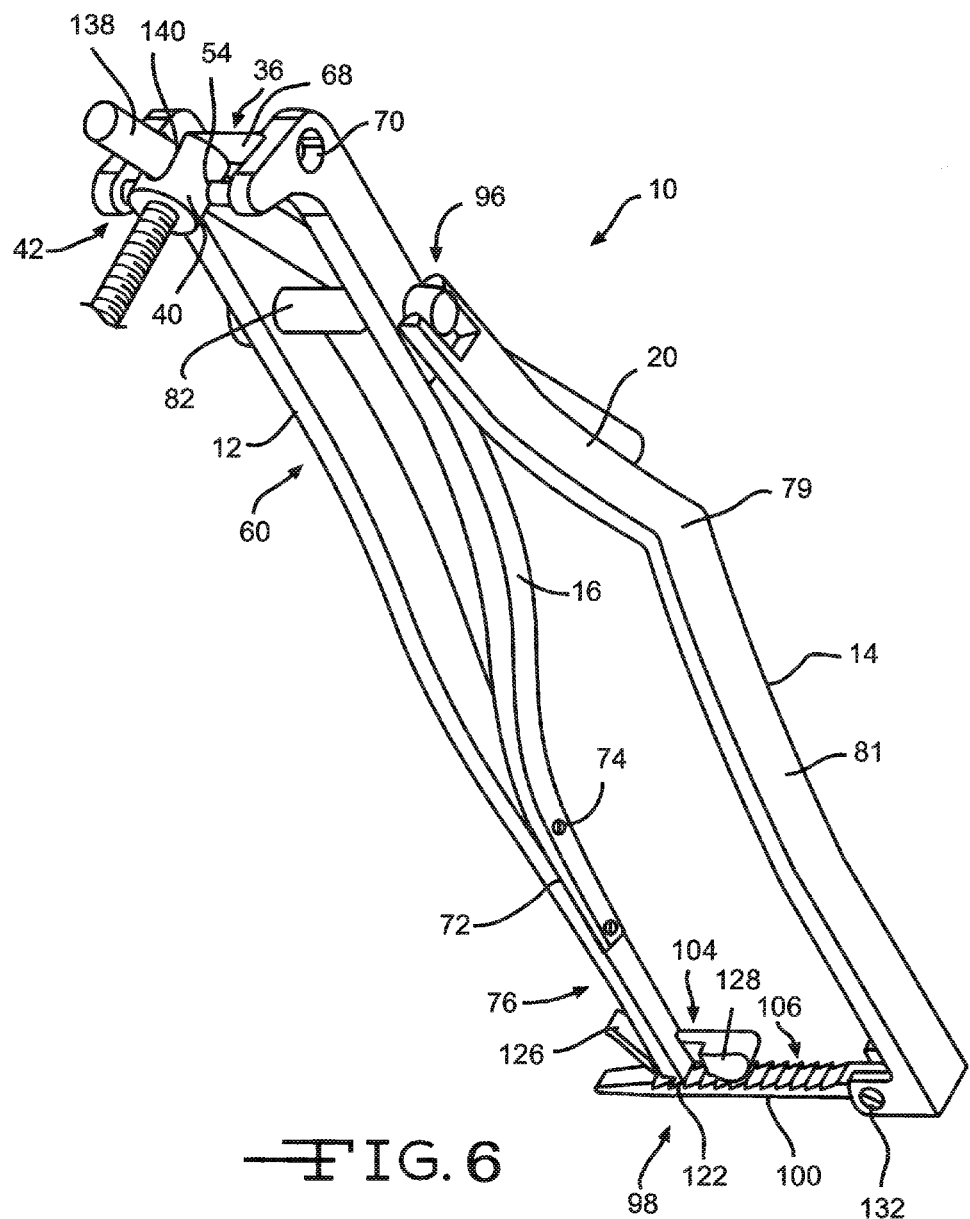
FIG. 6 illustrates the instrument of the present invention engaged with a pedicle screw and a surgical rod.

A gap 36 resides between the left and right prong portion 30a, 30b. The gap 36 is defined as the distance between an inner surface 38a, 38b of the distal ends of the right and left prong portions 30a, 30b. In an embodiment, this gap 36 has a first gap distance that ranges from about 1 cm to about 3 cm. The first gap distance is an open position that is wide enough to allow the passage of a contact portion such as a head 40 of a pedicle screw 42 to pass therebetween (FIG. 6). Additionally, the gap 36 has a second gap distance with a width that is wide enough to securely grasp the fixation element 42. In a preferred embodiment, the second gap distance has a width that is narrower than the first gap distance more preferably, the second gap distance ranges from about 0.5 cm to about 2 cm.

As illustrated in FIGS. 1, and 3-6, the left and intermediary arms 12, 16 comprise an outer surface 44, 46 separated from an inner surface 48, 50 these surfaces extend along the length of each arm 12, 16. In a preferred embodiment, these surfaces are planar. However it is contemplated that these surfaces may be curved. In an embodiment, a protrusion 52a, 52b extends from the respective inner surfaces 38a, 38b of the distal ends of the prongs 30a, 30b of the left and intermediary arms 12, 16. In a preferred embodiment, the protrusions 52a, 52b and prong portions 30a, 30b comprise a grasping portion 29. In a further preferred embodiment, the left and right protrusions 52a, 52b respectively, are positioned directly across from each other. These protrusions 52a, 52b are designed to contact and engage a recess 54 within the outer surface of the fixation element 42 such as a pedicle screw or hook. In a preferred embodiment, the protrusions 52a, 52b each have a protrusion height that ranges from about 0.1 cm to about 2 cm with a round cross section. However the cross section of the protrusion 52a, 52b is non-limiting and may comprise a rectangular, a hexagonal, a triangular or a round shape.

In an embodiment, the left arm 12 and the intermediary arm 16 have respective left arm and intermediary arm lengths 56, 58 that range from about 10 cm to about 25 cm. In a preferred embodiment, the left and intermediary arms 12, 16 are curved such that the distal end of the instrument 10 is narrower than its proximal end. The left arm 12 further comprises a left arm bend portion 60 positioned between the proximal end 24 and distal end 18 portions. In a preferred embodiment, the left arm bend portion 60 extends along the outer surface 44 with a left arm radius of curvature 62 that ranges about 5 cm to about 15 cm. Similarly, the intermediary arm 16 comprises an intermediary arm bend portion 64 positioned between the distal and proximal ends 22, 28. In a preferred embodiment, the intermediary arm bend portion 64 has an intermediary arm bend radius of curvature 66 that ranges from about 5 cm to about 20 cm. It is preferred that this radius of curvature 66 extends along the inner surface 50 of the intermediary arm 16.

As illustrated in FIGS. 1-2 and 4-6, a first pin 68 is positioned between the distal end portions 18, 22 of the left and intermediary arms 12, 16 where the arms form into respective prongs 30a, 30b. The first pin 68 is positioned proximal of the prong portions 52a, 52b and such that it extends from the left arm 12 to the intermediary arm 16. In a preferred embodiment, the first pin 68 extends from the left arm 12 through a width of the intermediary arm 16. More specifically, the first pin 68 is aligned with a through-bore 70 of the intermediary arm 16. The first pin 68 may be positioned such that the end of the pin fluidly contacts or is incorporated within the inner surface 38a of the distal end portion 18 of the left arm 12. Conversely, the first pin 68 may be positioned such that it extends from the intermediary arm 16 and is aligned with a through-bore (not shown) in the left arm 12. In either case, the first pin 68 is positioned to allow the opposing intermediary and left arms 16, 12 to move laterally towards each other.

At the proximal end portion of the instrument 10, the left arm 12 and the intermediary arm 16 are joined together at a joint 72. As illustrated in FIGS. 1-2, and 5-6, in a preferred embodiment, the joint 72 is established between the inner surface 48 of the proximal end portion of the left arm 12 and the inner surface 50 of the proximal end portion of the intermediary arm 16. A screw or rivet 74 may be used to secure these surfaces together. Alternatively, these surfaces 48, 50 may be joined together by an adhesive. The joint 72 formed between the proximal end portions 24, 28 of the left arm 12 and intermediary arm 16 creates a bias relationship between the two arms 12, 16 that imparts an opposing force between the two distal end prongs 30a, 30b. This design feature of joining the proximal end of the left arm to that of the intermediary arm 16 enables the inner surfaces of the opposing prongs 38a, 38b to come towards each other and return to their initial position when tension is released.

In a further embodiment, a handle portion 76 is formed at the proximal end of the instrument. In a preferred embodiment, the handle portion 76 is formed between the proximal ends 26, 24 of the right arm 14 and the left arm 12, respectively. When the handle portion is gripped by a user, an outer surface 78 of the right arm 14 and an outer surface 80 of the left arm 12 are held. The handle portion 76 is designed for use with either the right or left hands.

The right arm 14 extends from the proximal end of the instrument towards the distal end thereof. In a preferred embodiment, the right arm 14 extends to a region proximal of the distal end of the left arm 12. The right arm 14 is further positioned lateral, more preferably laterally right of the left and intermediary arms 12, 16. The distal end portion 20 of the right arm 14 is in contact with the outer surface 46 of the intermediary arm 16. As shown in FIGS. 1-2, and 5-6, the right arm 14 has an angled portion 79 positioned between distal end 20 and proximal end 26. More specifically, the angled portion 79 is an angled deviation off of a backwardly curved portion 81. In a preferred embodiment, the angled portion 79 defines the region at which the distal end portion 20 of the right arm 14 bends towards the intermediary arm 16.

In a preferred embodiment, a second pin 82, comprising a second pin, proximal end spaced from a second pin distal end, is positioned proximal of the first pin 68. The second pin 82 extends through the width of the left arm 12 and the width of the intermediary arm 16. More specifically, the second pin 82 is further positioned such that the distal end of the second pin 82 extends through the width of the left arm and through the width of the intermediary arm 16. The distal end of the second pin 82 connects with the distal end portion 20 of the right arm 14. A hook 84 residing at the distal end of the second pin 82 engages a cross bar 86 positioned at the distal end of the right arm 14. A pinhead 88 resides at the proximal end of the second pin 82. The pinhead 88 is preferably designed such that it is larger than the opening of the left arm 12 through which the second pin 82 extends. More preferably, the pinhead 88 is joined to the outer surface 44 of the left arm 12. This preferred embodiment prohibits the second pin 82 from being pulled through the width of the left arm 12, and more preferably, prevents the second pin 82 from moving with respect to the left arm. Alternately, the right arm 14 could be positioned on the left side of the instrument such that the distal end portion 20 of the right arm 14 contacts the left arm 12. In that case, the distal end of the second pin 82 would be positioned through the intermediary arm 16 and the left arm 12. In this alternative embodiment, the hook 84 is therefore connected to the distal end 20 of the right arm 14 now positioned on the left side of the instrument 10.

A fulcrum 90 (FIG. 5), located proximal of the cross bar 86, provides a contact point 92 between the distal end portion 20 of the right arm 14 to the outer surface 46 of the intermediary arm 16 or alternatively to the outer surface 44 of the left arm 12. The fulcrum 90, extending from an inner surface 94 of the distal end portion 20 of the right arm 14, provides a pivot point 96 by which the distal end 20 of the right arm 14 moves opposite that of the proximal end 26 of the right arm 14.

When the handle portion 26 is squeezed by a user, the proximal end 24 of the left arm 12 moves from a first left arm position to a second left arm position closer to the proximal end 26 of the right arm 14. More specifically, the outer surface 46 of the distal, end portion 22 of the intermediary arm 16 is compressed against the fulcrum 90, thereby moving the intermediary arm 16 closer to the left arm 12. As such, the opposing prong portions 30a, 30b move closer to each other. The second pin 82 in this case, enables the compression of the intermediary arm 16 towards the left arm 12.

In an alternative embodiment, the instrument could be designed such that the proximal end 26 of the right arm 14 moves toward the proximal end 24 of the left arm 12. In this case, the cross bar 86 located at the distal end of the right arm 14, moves rightwardly and laterally away from the left and intermediary arms 12, 16. This action thereby causes the second pin 82 to be pulled in a rightwardly lateral direction towards the intermediary arm 16. Therefore, the distal end portion 18 of the left arm 12 is brought closer to the distal end portion 22 of the intermediary arm 16 resulting in narrowing of the gap 36 between opposing prongs 30a, 30b.

In either case, the second pin 82 is kept in tension by the right arm 14. The pinhead 88, which is in contact with the outer surface 44 of the left arm 12, engages the left arm 12 and moves with the left arm 12 closer to the intermediary arm 16. Since the pinhead 88 is larger than the opening through which the second pin 82 extends through the left arm 12, the second pin 82 is prevented from being pulled through the left arm 12. Therefore, the left arm 12 moves closer to the intermediary arm 16. As a result, the first prong 30a residing at the distal end portion 18 of the left arm 12 moves closer to the opposing second prong 30b, thereby reducing the gap 36 therebetween. As the distance of the gap 36 narrows, the grasping portion closes and the respective opposing protrusions 52a, 52b engage with the outer surface of the fixation element 42, i.e. pedicle screw, hook or the like.

In an embodiment illustrated in FIGS. 1-2, and 5-6, the proximal end of the instrument 10 comprises a locking mechanism 98. The locking mechanism 98 preferably comprises a ratchet post 100, and a corresponding "V" groove 102 positioned at the proximal end of the left arm 12. In addition, a pivotable release lever 104 is provided to disengage the locking mechanism 98. The locking and release mechanisms 98, 104 respectively, provide a quick, easy and stable means of locking and releasing the handle 76 into and from a fixed position, thereby locking and releasing the grasping portion 29 at the corresponding distal end of the instrument 10.

Figure 5:
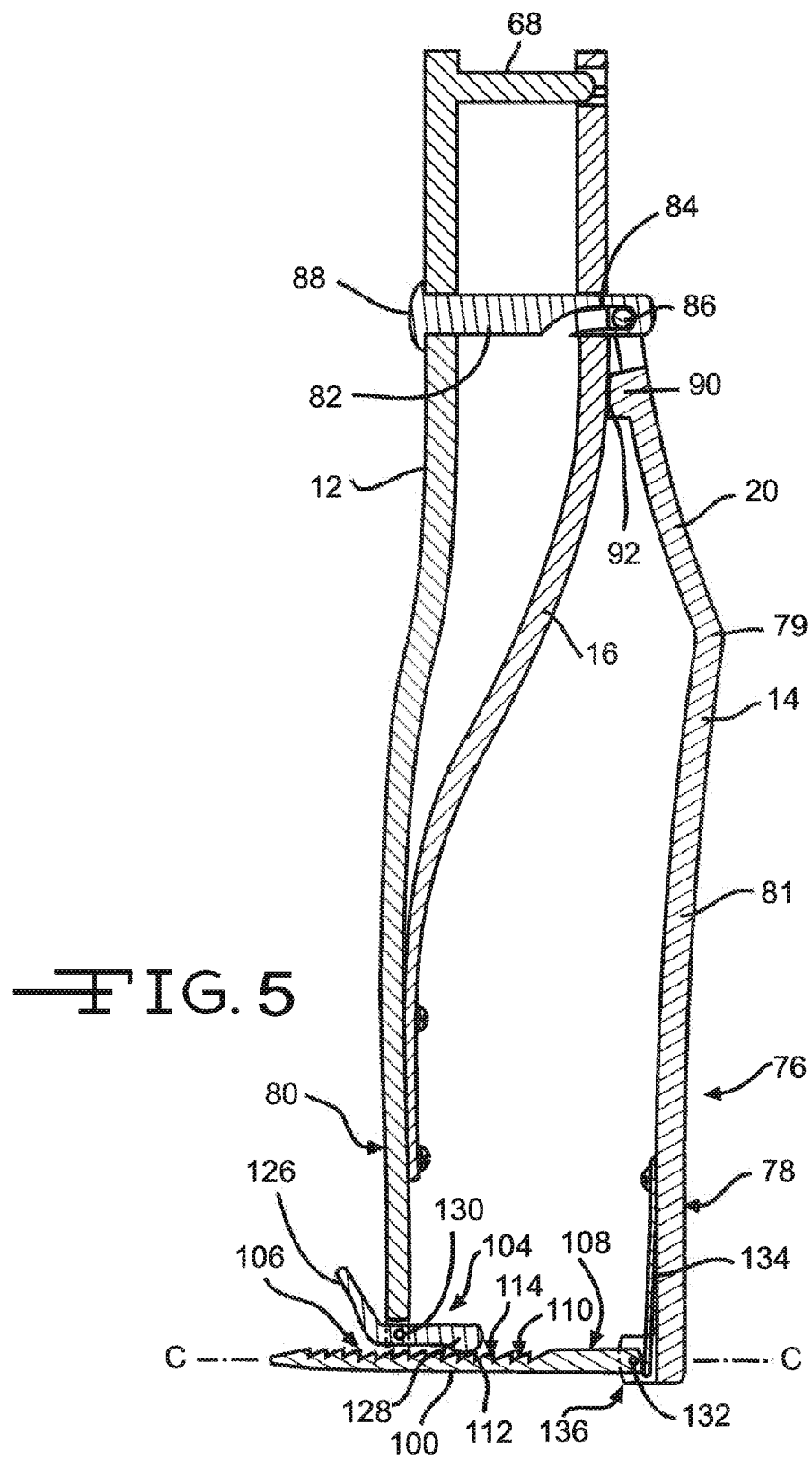
FIG. 5 shows a cross sectional view of the instrument taken along line 5-5 of FIG. 3.

In a preferred embodiment, the ratchet post 100 is oriented about perpendicular to the proximal ends 24, 26 of both the left and right arms 12, 14. In addition, the ratchet post 100 has a series of teeth that extend from a top surface 108 thereof. The teeth 106 are further positioned such that each of them is angled toward the proximal end 26 of the opposing arm, i.e.

the right arm 14. In a preferred embodiment, each of the teeth 106 comprise a first surface 110 and a second surface 112 that meet at a tooth apex 114 (FIG. 5). The first teeth surface 110 is preferably angled at about 45° with respect to a ratchet post longitudinal axis C-C, and the second teeth surface 112 is about perpendicular to the top surface 108 of the ratchet post 100.

The "V" groove 102 comprises a first surface 116, a second surface 118 and a groove opening 120 therebetween. In a preferred embodiment, the groove opening 120 is positioned facing towards the left side, away from the first surface of the teeth 106. The "V" groove 102 further comprises a teeth contacting surface 122 that resides on the backside of the first groove surface 116. The groove teeth contacting surface 122 and the groove first surface 116 form a wedge 124 with a pointed end that extends to the proximal end of the instrument 10. The teeth 106 of the ratchet post 100 and the wedge 124 of the groove 102 are therefore in opposing orientations.

As the handle portion 76 is closed, the left arm 12, moves closer to the opposing right arm 14. The teeth contacting surface 122 of the groove 102, thusly rides up the first tooth surface 110 towards the tooth apex 114. As the groove surface 122 moves past the apex 114, the wedge 124 of the groove 102 becomes entrapped between the second tooth surface 112 of the previous tooth and the first surface 110 of the adjacent tooth. Thus, the arms 12, 14 of the handle 76 and the opposing prongs 30a, 30b of the grasping portion 29 at the distal end of the instrument 10 are prevented from moving apart in opposite directions. If desired, the user can continue to squeeze the arms of the handle 76 together which brings the opposing prongs 30a, 30b closer together.

The pivotable release lever 104 is positioned at the proximal end of the left arm 12. The lever 104 comprises a thumb rest 126 opposite that of a bulbous portion 128. The lever 104 is preferably attached to the proximal end of the left arm 12 via a lever connection pin 130 which enables the lever 104 to rock or pivot back and forth. The lever pin 130 is located between the thumb rest 126 and the bulbous end 128. The connection pin 130 provides a lever pivot point, which enables the bulbous end 128 to move in an opposite direction to that of the thumb rest 126.

In a preferred embodiment, the release lever 104 is activated by pressing the thumb rest 126 towards the outer surface 44 of the left arm 12. As the thumb rest 126 is depressed, the bulbous end portion 128 contacts the teeth 106 of the ratchet post 100. As the bulbous end 128, is further pressed against the ratchet post 100, the ratchet post 100 moves in a proximal direction away from the groove 102 of the left arm, 12 thereby disengaging the teeth 106 of the ratchet post 100 from the groove 102 of the arm 12. Once the groove 102 is disengaged from the teeth 106 of the ratchet post 100, the opposing prongs 30a, 30b of the grasping portion 29 return to the first gap distance sufficient to allow the protrusions 50a, 50b to disengage from the fixation element 42.

In a preferred embodiment, the ratchet post 100 is joined to the end of the right arm 14 by a ratchet post pin 132. A biasing tab 134 is positioned along the inside surface 94 of the right arm 14. The distal end of the biasing tab 134 further extends within an aperture 136 between the inner surface 94 of the right arm 14 and the proximal end of the ratchet post 100. The biasing tab 134 allows the ratchet post 100 to pivot about pin 132, and in addition, provides a force against the proximal end of the ratchet post 100 to ensure that the post is in a preferred perpendicular orientation with respect to the inner surface 94 of the right arm 14.

FIG. 6 illustrates the present invention engaged with a pedicle screw 42 fixation element. As shown, the opposing protrusions 52a, 52b are positioned within respective recesses only one shown) of the outer surface of the pedicle screw 42. A rod 138 is shown extending along longitudinal axis A-A, perpendicular to the span of the first and second pins 68, 82. The end of the rod 138 is further positioned within an inlet 140 of the pedicle screw 42.

In operation, the opposing first and second prongs 30a, 30b of the grasping portion 29 are first positioned about the head of the fixation element such that the head lies within the gap 36 between the prongs. Once the opposing prongs are correctly positioned, the handle portion is squeezed, bringing the proximal end portion of the left arm 12 closer to the proximal end portion of the right arm 14. This action brings the opposing first and second prongs 30a, 30b of the grasping portion 29 closer together, compressing against an outer surface of the fixation element 42. At the same time, the wedge portion 124 of the groove 102 at the proximal end of the left arm 12, mates with the teeth 106 of the ratchet post 100 which prevents the proximal end portions of the left and right arms 12, 14 from moving apart and in so doing, prevents the first and second prongs 30a, 30b of the distal end grasping portion 29 from also moving apart.

The surgical rod 138 which has been positioned longitudinally along axis A-A and between the span of the first and second pins 68, 82, is urged within the inlet 140 of the fixation element 42. Specifically, the surgical rod 138 is urged within the inlet 140 of the fixation element 42 by rocking the instrument 10 in an upwardly and downwardly direction about the head 40 of the fixation element 42, similarly to that of a hinging motion. The hinging motion of the instrument 10 guides the surgical rod 138 within the inlet 140 of the fixation element 42. Once the end of the surgical rod 138 is correctly positioned, a setscrew (not shown) is positioned at the top of the fixation element 42, securing the end of the surgical rod 138 therewithin. The thumb rest 126 of the pivotable releasing lever 104 is then depressed, which, disengages the "V groove" 102 from the teeth 106 of the ratchet post 100 releasing the locking mechanism 98, and thus allowing the opposing handle arms 12, 14 and opposing first and second prongs 30a, 30b, to return to their open position. The process is then repeated to secure the other end of the surgical rod 138.

It is intended that the foregoing description and example only be illustrative of the present invention and that the present invention is limited only by the following appended claims.

What is claimed is:

1. An orthopedic instrument, comprising:
   a) a left arm having a left arm proximal end spaced from a left arm distal end, a right arm having a right arm proximal end spaced from a right arm distal end, and an intermediary arm having an intermediary arm proximal end spaced from an intermediary arm distal arm, wherein the intermediary arm proximal end is connected to the left arm with the right arm distal end contacting an intermediary arm outer surface distal the connection of the intermediary arm to the left arm, thereby providing a fulcrum point between the right and intermediary arms;
   b) a grasping portion comprised of opposing first and second prongs, the first prong extending from the distal end of the left arm and the second prong extending from the distal end of the intermediary arm;
   c) a handle portion formed by the proximal ends of the left and right arms; and
   d) wherein when the proximal ends of the opposing left and right arms are brought towards each other, the right arm distal end contacts the intermediary arm outer surface at the fulcrum point, the distal end of the intermediary arm movable toward the opposing distal end of the left arm, thus the opposing first and second prongs at the distal ends of the respective left and intermediary arms are movable from a first prong position spaced from each other to a second prong position closer than the first position.

2. The instrument of claim 1 wherein a protrusion extends from an inner surface of at least one of the first or second prongs.

3. The instrument of claim 1 wherein the left and intermediary arms each have a curvature portion that is intermediate their respective proximal and distal ends.

4. The instrument of claim 3 wherein the curvatures of the left and intermediary arms curve in a similar direction.

5. The instrument of claim 3 wherein the curvature of the left arm has a left arm radius of curvature that ranges from about 5 cm to about 15 cm.

6. The instrument of claim 3 wherein the curvature of the intermediary arm has an intermediary arm radius of curvature that ranges from about 5 cm to about 20 cm.

7. The instrument of claim 1 wherein the right arm comprises an angled deviation extending toward the intermediary arm.

8. The instrument of claim 1 wherein a first pin extends between the left arm and through a width of the intermediary arm.

9. The instrument of claim 1 wherein a second pin is positioned proximal of the first pin, the second pin comprising a second pin proximal end supported by the left arm and a second pin distal end, the second pin distal end having a hook that extends through a width of the intermediary arm to connect to a cross bar residing at the distal end of the right arm.

10. The instrument of claim 1 wherein the proximal end of the intermediary arm is joined to an inner surface of the proximal end of the left arm.

11. The instrument of claim 1 wherein a ratchet post is positioned about perpendicular between the proximal ends of the left and right arms, the ratchet post comprising a plurality of teeth extending from a top surface of the ratchet post.

12. The instrument of claim 1 wherein the proximal end of the left arm comprises a "V" groove, the "V" groove further comprising a wedge portion that is positionable between the teeth of the ratchet post.

13. The instrument of claim 1 wherein a pivotable release lever comprising a thumb rest spaced from a bulbous end resides at the proximal end of the left arm, the release lever being pivotable about a connection pin that attaches to the proximal end of the left arm to thereby cause the bulbous end to move the proximal end of the left arm out of a ratchet relationship with a ratchet post pivotably connected to the proximal end of the right arm.

14. The orthopedic instrument of claim 1 wherein the intermediary arm connects to a cross bar residing at the distal end of the right arm.

15. An orthopedic rocker instrument, comprising:
a) a grasping portion positioned at a distal end of the instrument, the grasping portion comprising opposing first and second prongs spaced apart by a gap, the first prong connected to a left arm and the second prong connected to an intermediary arm, a first pin supported by the left arm and extending through an opening in the intermediary arm;
b) a handle portion residing at a proximal end of the instrument, the handle portion comprising a proximal end of the left arm and an opposing proximal end of a right arm, and wherein a proximal end of the intermediary arm is joined to an inner surface of the proximal end of the left arm;
c) a ratchet post positioned about perpendicular between the proximal ends of the left and right arms, the ratchet post comprising a series of teeth extending along a top surface of the ratchet post; and
d) wherein the opposing proximal ends of the left and right arms of the handle portion are movable toward each other with the first pin extendable through a width of the intermediary arm as the gap between the opposing first and second prongs becomes narrower.

16. The instrument of claim 15 wherein a protrusion extends from an inner surface of at least one of the first and second prongs.

17. The instrument of claim 15 wherein a second pin is positioned proximal of the first pin, the second pin comprising a second pin proximal end supported by the left arm and a second pin distal end, the second pin distal end having a hook that extends through a width of the intermediary arm to connect to a cross bar residing at the distal end of the right arm.

18. The instrument of claim 17 wherein the proximal end of the left arm of the handle portion is movable closer to the proximal end of the right arm, and wherein an outer surface of the intermediary arm contacts a fulcrum point extending from an inner surface of the distal end portion of the right arm, the distal end of the intermediary arm moveable toward the opposing distal end of the left arm, thus decreasing the gap between the respective distal ends of the left and intermediary arms.

19. The instrument of claim 15 wherein the proximal end of the left arm comprises a "V" groove, the "V" groove further comprising a wedge portion that is positionable between the teeth of the ratchet post.

20. The instrument of claim 15 wherein a pivotable release lever comprising a thumb rest spaced from a bulbous end resides at the proximal end of the left arm, the lever being pivotable about a connection pin that attaches to the proximal end of the left arm to thereby cause the bulbous end to move the proximal end of the left arm out of a ratchet relationship with a ratchet post pivotably connected to the proximal end of the right arm.

21. An orthopedic instrument, comprising:
a) left arm having a left arm proximal end spaced from a left arm distal end, a right arm having a right arm proximal end spaced from a right arm distal end, and an intermediary arm having an intermediary arm proximal end spaced from an intermediary arm distal end, wherein the intermediary arm proximal end is connected to the left arm with the right arm distal end contacting an intermediary arm outer surface distal the connection of the intermediary arm to the left arm, thereby providing a fulcrum point between the right and intermediary arms, a first pin residing between the left arm and the intermediary arm;
b) a grasping portion comprised of opposing first and second prongs, the first prong extending from the distal end of the left arm and the second prong extending from the distal end of the intermediary arm;
c) a second pin positioned proximal of the first pin, the second pin comprising a second pin proximal end supported by the left arm and a second pin distal end, the second pin distal end having a hook that extends through a width of the intermediary arm to connect to the distal end of the right arm;
d) a handle portion formed by the proximal ends of the left and right arms; and e) wherein when the proximal ends of the opposing left and right arms are brought toward each other, the first pin extends through a width of the intermediary arm, and wherein the right arm distal end contacts the intermediary arm at the fulcrum point, the distal end of the intermediary arm movable toward the opposing distal end of the left arm, thus the opposing first and second prongs at the distal ends of the respective left and intermediary arms are movable from a first prong position spaced from each other to a second prong position closer than the first position.

22. The orthopedic instrument of claim 21 wherein the intermediary arm connects to a cross bar residing at the distal end of the right arm.

\* \* \* \* \*

UNITED STATES PATENT AND TRADEMARK OFFICE
CERTIFICATE OF CORRECTION

| | | |
|---|---|---|
| PATENT NO. | : 8,777,953 B1 | Page 1 of 1 |
| APPLICATION NO. | : 13/267049 | |
| DATED | : July 15, 2014 | |
| INVENTOR(S) | : Farid B. Khalili | |

It is certified that error appears in the above-identified patent and that said Letters Patent is hereby corrected as shown below:

In the Claims

Column 10, line 45 (Claim 21, line 2) after "a)" insert --a--

Signed and Sealed this
Twenty-fourth Day of February, 2015

Michelle K. Lee
*Deputy Director of the United States Patent and Trademark Office*